US006579539B2

(12) United States Patent
Lawson et al.

(10) Patent No.: US 6,579,539 B2
(45) Date of Patent: *Jun. 17, 2003

(54) DUAL MODE ANTIMICROBIAL COMPOSITIONS

(75) Inventors: Glenn Lawson, Oxford, GA (US); Richard Terry, Conyers, GA (US)

(73) Assignee: C. R. Bard, Inc., NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/469,909

(22) Filed: Dec. 22, 1999

(65) Prior Publication Data
US 2002/0094322 A1 Jul. 18, 2002

(51) Int. Cl.$^7$ .......................... A01N 59/16; A61K 33/38
(52) U.S. Cl. ....................... 424/618; 424/600; 424/617; 424/422; 424/78.08; 424/78.17; 427/2.1; 427/2.3; 604/265
(58) Field of Search .................. 427/2.1, 2.3; 604/265; 523/111, 122; 424/78.08, 422, 430, 78.17, 618

(56) References Cited

U.S. PATENT DOCUMENTS

| | | |
|---|---|---|
| 1,557,234 A | 10/1925 | Bechhold |
| 1,642,089 A | 9/1927 | Schreier |
| 1,691,755 A | 11/1928 | Bilttner |
| 2,283,883 A | 5/1942 | Conconi ..................... 210/205 |
| 2,459,896 A | 1/1949 | Schwarz ................... 117/138.5 |
| 2,653,893 A | 9/1953 | Romans ....................... 167/14 |
| 2,689,809 A | 9/1954 | Fessler ..................... 117/138.5 |
| 2,785,106 A | 3/1957 | Mendelsohn ................. 167/84 |
| 2,791,518 A | 5/1957 | Stokes, Jr. et al. .......... 117/120 |
| 2,813,056 A | 11/1957 | Davis et al. .................. 167/14 |
| 2,813,059 A | 11/1957 | Davis et al. .................. 167/72 |
| 2,822,289 A | 2/1958 | Millard, Jr. ................... 117/35 |
| 2,879,175 A | 3/1959 | Umblia et al. ................ 117/35 |
| 2,947,282 A | 8/1960 | Brown ..................... 119/14.47 |
| 3,092,552 A | 6/1963 | Romans ....................... 167/72 |
| 3,184,376 A | 5/1965 | Degoli ........................ 167/14 |
| 3,300,336 A | 1/1967 | Gagliardi et al. ......... 117/138.5 |
| 3,350,265 A | 10/1967 | Rubinstein et al. ........ 167/38.6 |
| 3,380,848 A | 4/1968 | Horowitz .................... 117/113 |
| 3,396,727 A | 8/1968 | Mount ........................ 128/349 |
| 3,434,869 A | 3/1969 | Davidson ..................... 117/94 |
| 3,561,995 A | 2/1971 | Wu et al. ...................... 117/47 |
| 3,566,874 A | 3/1971 | Shepherd et al. ........... 128/349 |
| 3,598,127 A | 8/1971 | Wepsic ....................... 128/349 |
| 3,639,575 A | 2/1972 | Schmolka .................... 424/78 |
| 3,695,921 A | 10/1972 | Shepherd et al. ............. 117/72 |
| 3,705,938 A | 12/1972 | Hyman et al. ................ 424/19 |
| 3,734,897 A | 5/1973 | Stoy .......................... 260/79.3 |
| 3,822,238 A | 7/1974 | Blair et al. ............. 260/75 NK |
| 3,841,881 A | 10/1974 | Feldstein et al. .............. 106/1 |
| 3,877,965 A | 4/1975 | Broadbent et al. .......... 427/304 |
| 3,953,545 A | 4/1976 | Stoy ............................. 260/898 |
| 3,975,350 A | 8/1976 | Hudgin et al. .............. 260/30.4 |
| 4,027,393 A | 6/1977 | Ellis et al. .................... 32/10 A |
| 4,054,139 A | 10/1977 | Crossley ..................... 128/260 |
| 4,156,066 A | 5/1979 | Gould ........................... 528/73 |
| 4,156,067 A | 5/1979 | Gould ........................... 528/73 |
| 4,180,602 A | 12/1979 | Schiavone .................. 427/306 |
| 4,237,229 A | 12/1980 | Hartdegen et al. .......... 435/182 |
| 4,253,463 A | 3/1981 | Kim ............................ 128/348 |
| 4,255,550 A | 3/1981 | Gould ........................... 528/44 |
| 4,284,444 A | 8/1981 | Bernstein et al. .............. 156/60 |
| 4,359,558 A | 11/1982 | Gould et al. ................. 525/454 |
| 4,404,197 A | 9/1983 | Fox, Jr. et al. .............. 424/229 |
| 4,407,865 A | 10/1983 | Nice .......................... 427/217 |
| 4,408,023 A | 10/1983 | Gould et al. ................. 525/454 |
| 4,411,648 A | 10/1983 | Davis et al. ................... 604/21 |
| 4,419,495 A | 12/1983 | Davis ......................... 525/109 |
| 4,421,660 A | 12/1983 | Solc nee Hajna ......... 252/62.54 |
| 4,424,305 A | 1/1984 | Gould et al. ................. 525/127 |
| 4,436,855 A | 3/1984 | Higgins et al. .............. 524/145 |
| 4,439,583 A | 3/1984 | Gould et al. ................. 525/127 |
| 4,439,585 A | 3/1984 | Gould et al. ................. 525/127 |

(List continued on next page.)

FOREIGN PATENT DOCUMENTS

| | | |
|---|---|---|
| DE | 002350050 | 4/1974 |
| DE | 3228849 | 2/1984 |
| EP | 0 206 024 A2 | 12/1986 |
| EP | 0 301 717 B1 | 11/1991 |
| EP | 0 251 783 B1 | 4/1993 |
| EP | 0 318 258 B1 | 4/1993 |
| EP | 0 328 421 B1 | 4/1993 |
| EP | 0 379 269 B1 | 3/1994 |
| EP | 0 400 349 B1 | 2/1996 |
| GB | 777679 | 6/1957 |
| JP | 359218157 A | 8/1990 |
| JP | 402200269 | 8/1990 |
| JP | 4002877 A2 | 1/1992 |
| JP | 4076518 A2 | 3/1992 |
| JP | 4173712 A2 | 6/1992 |
| WO | WO 81/02667 | 10/1981 |
| WO | WO 84/01721 | 5/1984 |
| WO | WO 89/01793 | 3/1989 |

OTHER PUBLICATIONS

Bach, A. et al "Prevention of bacterial colonization of intravenous catheters by antiseptic impregnation of polyurethane polymers" (1994) J. Antimicrobial Chemotherapy 33: 969–978.

(List continued on next page.)

Primary Examiner—Thurman K. Page
Assistant Examiner—Liliana Di Nola-Baron
(74) Attorney, Agent, or Firm—Morgan & Finnegan, LLP

(57) ABSTRACT

The present invention provides compositions which reduce the possibility of inducing microbial resistance. The compositions comprise a fast-acting antimicrobial agent and a long-lasting antimicrobial agent. The combined effect of the antimicrobial agents reduces microbial infection and resistance. Articles comprising the compositions of the present invention and methods for their manufacture are also provided.

34 Claims, No Drawings

U.S. PATENT DOCUMENTS

| | | | |
|---|---|---|---|
| 4,442,125 A | 4/1984 | Thiele | 424/318 |
| 4,443,577 A | 4/1984 | Higgins et al. | 524/590 |
| 4,454,309 A | 6/1984 | Gould et al. | 525/454 |
| 4,476,590 A | 10/1984 | Scales et al. | 3/1.91 |
| 4,483,688 A | 11/1984 | Akiyama | 604/265 |
| 4,487,810 A | 12/1984 | Ascarelli et al. | 428/461 |
| 4,496,535 A | 1/1985 | Gould et al. | 424/19 |
| 4,515,593 A | 5/1985 | Norton | 604/265 |
| 4,525,410 A | 6/1985 | Hagiwara et al. | 428/198 |
| 4,539,234 A | 9/1985 | Sakamoto et al. | 427/393.5 |
| 4,539,267 A | 9/1985 | Sederquist | 427/393.5 |
| 4,540,631 A | 9/1985 | Boultinghouse | 428/419 |
| 4,542,169 A | 9/1985 | Costerton | 523/121 |
| 4,559,033 A | 12/1985 | Stephen et al. | 604/49 |
| 4,563,485 A | 1/1986 | Fox, Jr. et al. | 523/113 |
| 4,564,361 A | 1/1986 | Akiyama | 604/265 |
| 4,569,673 A | 2/1986 | Tesi | 604/20 |
| 4,581,028 A | 4/1986 | Fox, Jr. et al. | 623/2 |
| 4,592,920 A | 6/1986 | Murtfeldt | 427/2 |
| 4,603,152 A | 7/1986 | Laurin et al. | 604/265 |
| 4,612,337 A | 9/1986 | Fox, Jr. et al. | 523/113 |
| 4,615,705 A | 10/1986 | Scales et al. | 623/11 |
| 4,642,104 A | 2/1987 | Sakamoto et al. | 604/264 |
| 4,675,347 A | 6/1987 | Mochizuki et al. | 523/122 |
| 4,677,143 A | 6/1987 | Laurin et al. | 532/122 |
| 4,689,375 A | 8/1987 | Lauterbach | 525/471 |
| 4,728,323 A | 3/1988 | Matson | 604/304 |
| 4,729,914 A | 3/1988 | Kliment et al. | 428/36 |
| 4,738,782 A | 4/1988 | Yamauchi et al. | 210/650 |
| 4,769,013 A | 9/1988 | Lorenz et al. | 604/265 |
| 4,775,585 A | 10/1988 | Hagiwara et al. | 428/323 |
| 4,789,720 A | 12/1988 | Teffenhart | 528/76 |
| 4,810,543 A | 3/1989 | Gould et al. | 428/35.7 |
| 4,810,582 A | 3/1989 | Gould et al. | 428/423.1 |
| 4,820,292 A | 4/1989 | Korol et al. | 435/32 |
| 4,849,223 A | 7/1989 | Pratt et al. | 424/409 |
| 4,871,790 A | 10/1989 | Lamanna et al. | 523/333 |
| 4,879,109 A | 11/1989 | Hunter | 424/83 |
| 4,885,855 A | 12/1989 | Marks, Sr. et al. | 40/301 |
| 4,886,505 A | 12/1989 | Haynes et al. | 604/265 |
| 4,902,503 A | 2/1990 | Umemura et al. | 424/83 |
| 4,906,464 A | 3/1990 | Yamamoto et al. | 424/78 |
| 4,911,898 A | 3/1990 | Hagiwara et al. | 423/118 |
| 4,911,899 A | 3/1990 | Hagiwara et al. | 423/118 |
| 4,923,450 A | 5/1990 | Maeda et al. | 604/265 |
| 4,925,668 A | 5/1990 | Khan et al. | |
| 4,933,178 A | 6/1990 | Capelli | 424/78 |
| 4,937,273 A | 6/1990 | Okuyama et al. | 521/119 |
| 4,938,955 A | 7/1990 | Niira et al. | 424/79 |
| 4,938,958 A | 7/1990 | Niira et al. | 424/79 |
| 4,959,268 A | 9/1990 | Hagiwara et al. | 428/403 |
| 4,973,320 A | 11/1990 | Brenner et al. | 604/265 |
| 4,990,144 A | 2/1991 | Blott | 604/304 |
| 4,999,210 A | 3/1991 | Solomon et al. | |
| 5,013,306 A | 5/1991 | Solomon et al. | 604/265 |
| 5,019,096 A | 5/1991 | Fox, Jr. et al. | 623/1 |
| 5,047,448 A | 9/1991 | Tanaka et al. | 523/122 |
| 5,049,140 A | 9/1991 | Brenner et al. | 604/266 |
| 5,064,599 A | 11/1991 | Ando et al. | 264/237 |
| 5,089,205 A | 2/1992 | Huang et al. | 264/255 |
| 5,091,442 A | 2/1992 | Milner | 523/122 |
| 5,094,847 A | 3/1992 | Yazaki et al. | 424/618 |
| 5,100,671 A | 3/1992 | Maeda et al. | 424/443 |
| 5,102,401 A | 4/1992 | Lambert et al. | 604/264 |
| 5,120,816 A | 6/1992 | Gould et al. | 528/76 |
| 5,142,010 A | 8/1992 | Olstein | 526/248 |
| 5,151,122 A | 9/1992 | Atsumi et al. | 106/35 |
| 5,165,952 A | 11/1992 | Solomon et al. | 427/2 |
| 5,180,402 A | 1/1993 | Kubota et al. | 8/490 |
| 5,180,585 A | 1/1993 | Jacobson et al. | 424/405 |
| 5,201,724 A | 4/1993 | Hukins et al. | |
| 5,208,016 A | 5/1993 | Ohmae et al. | 424/78.27 |
| 5,244,667 A | 9/1993 | Hagiwara et al. | 424/409 |
| 5,290,585 A | 3/1994 | Elton | 427/2 |
| 5,320,908 A | 6/1994 | Sodervall et al. | 428/461 |
| 5,322,520 A | 6/1994 | Milder | 604/265 |
| 5,322,887 A | 6/1994 | Howell et al. | 524/781 |
| 5,326,567 A | 7/1994 | Capelli | 424/405 |
| 5,328,698 A * | 7/1994 | Onwumere et al. | 424/486 |
| 5,328,954 A | 7/1994 | Sarangapani | 524/589 |
| 5,331,027 A | 7/1994 | Whitbourne | 524/37 |
| 5,334,691 A | 8/1994 | Gould et al. | 528/76 |
| 5,344,455 A | 9/1994 | Keogh et al. | |
| 5,366,505 A | 11/1994 | Farber | 623/11 |
| 5,395,651 A | 3/1995 | Sodervall et al. | 427/304 |
| 5,405,644 A | 4/1995 | Ohsumi et al. | 427/2.31 |
| 5,413,789 A | 5/1995 | Hagiwara et al. | 424/409 |
| 5,436,282 A | 7/1995 | Gustafsson et al. | 523/102 |
| 5,439,866 A | 8/1995 | Sakoda et al. | 502/407 |
| 5,444,134 A | 8/1995 | Matsumoto | 526/159 |
| 5,451,424 A | 9/1995 | Solomon et al. | 427/2.1 |
| 5,466,726 A | 11/1995 | Inoue et al. | 523/122 |
| 5,468,562 A | 11/1995 | Farivar et al. | |
| 5,468,738 A | 11/1995 | Okabayashi et al. | 514/63 |
| 5,474,797 A | 12/1995 | Sioshansi et al. | |
| 5,478,563 A | 12/1995 | Erami | 424/409 |
| 5,492,763 A | 2/1996 | Barry et al. | |
| 5,500,253 A | 3/1996 | Sanduja et al. | 427/385.5 |
| 5,503,840 A | 4/1996 | Jacobson et al. | 424/421 |
| 5,516,480 A | 5/1996 | Krall et al. | 264/343 |
| 5,518,730 A | 5/1996 | Fuisz | 424/426 |
| 5,520,664 A | 5/1996 | Bricault, Jr. et al. | |
| 5,554,147 A | 9/1996 | Batich et al. | 604/890.1 |
| 5,556,618 A | 9/1996 | Ando et al. | 424/78.08 |
| 5,556,699 A | 9/1996 | Niira et al. | 428/323 |
| 5,563,233 A | 10/1996 | Reich et al. | 528/76 |
| 5,567,495 A | 10/1996 | Modak et al. | |
| 5,607,417 A | 3/1997 | Batich et al. | 604/890.1 |
| 5,607,683 A | 3/1997 | Capelli | 424/405 |
| 5,614,568 A | 3/1997 | Mawatari et al. | 523/122 |
| 5,616,338 A | 4/1997 | Fox, Jr. et al. | |
| 5,618,762 A | 4/1997 | Shirakawa et al. | 501/1 |
| 5,624,704 A | 4/1997 | Darouiche et al. | 427/2.24 |
| 5,648,558 A | 7/1997 | Hatano et al. | 568/618 |
| 5,662,913 A | 9/1997 | Capelli | 424/405 |
| 5,707,366 A | 1/1998 | Solomon et al. | |
| 5,709,672 A | 1/1998 | Illner | |
| 5,709,870 A | 1/1998 | Yoshimura et al. | 424/404 |
| 5,723,110 A | 3/1998 | Yamamoto et al. | 424/65 |
| 5,730,995 A | 3/1998 | Shirono et al. | 424/404 |
| 5,736,591 A | 4/1998 | Dunn | 523/122 |
| 5,739,178 A | 4/1998 | Powell et al. | 523/122 |
| 5,741,886 A | 4/1998 | Stockel et al. | 528/422 |
| 5,744,151 A | 4/1998 | Capelli | 424/405 |
| 5,747,178 A | 5/1998 | Sodervall et al. | |
| 5,772,640 A | 6/1998 | Modak et al. | 604/265 |
| 5,788,687 A | 8/1998 | Batich et al. | 604/890.1 |
| 5,798,115 A | 8/1998 | Santerre et al. | |
| 5,807,306 A | 9/1998 | Shapland et al. | 604/21 |
| 5,811,151 A | 9/1998 | Hendriks et al. | 427/2.24 |
| 5,817,325 A | 10/1998 | Sawan et al. | 424/411 |
| 5,820,607 A | 10/1998 | Tcholakian et al. | |
| 5,824,407 A | 10/1998 | Hayashi et al. | 428/318.8 |
| 5,827,524 A | 10/1998 | Hagiwara et al. | 424/409 |
| 5,833,665 A | 11/1998 | Bootman et al. | 604/180 |
| 5,840,338 A | 11/1998 | Roos et al. | 424/488 |
| 5,844,013 A | 12/1998 | Kenndoff et al. | 521/137 |
| 5,848,995 A | 12/1998 | Walder | 604/265 |
| 5,849,311 A | 12/1998 | Sawan et al. | 424/406 |
| 5,853,745 A | 12/1998 | Darouiche | |
| 5,861,032 A | 1/1999 | Subramaniam | 623/11 |

| | | |
|---|---|---|
| 5,869,073 A | 2/1999 | Sawan et al. |
| 5,902,283 A | 5/1999 | Darouiche et al. |
| 5,965,636 A | 10/1999 | Lark .......................... 523/207 |
| 5,976,562 A | 11/1999 | Krall et al. ................. 424/402 |
| 5,993,910 A | 11/1999 | Carre et al. ................. 427/387 |
| 5,998,504 A | 12/1999 | Groth et al. ................ 523/213 |
| 6,013,106 A | 1/2000 | Tweden et al. ............... 623/66 |

OTHER PUBLICATIONS

CAS Abstract 115:185307q *Fibers having antibacterial properties.*

CAS Abstract 79: 105832g, *Copolymers or mixtures of homopolymers with oligodynamic and catalytic effects.*

Abstract, Derwent Publications Ltd., XP002137135 & JP 03 063061, (1991).

Frarah, S.R., et al., "The production of antibacterial tubing, sutures, and bandages by in situ preception of metallic salts," Can J. Microbiol (1991) 37, vol. 6, pp. 445–459.

Hoffman, A.S., "Synthetic Polymeric Biomaterials", Am. Chem Society(1984).

Johnson, J. P., "Prevention of catheter–associated urinary tract infection with a silver oxide–coated urinary catheter; clinical and microbilogic correlates," J. Infect Dis. (1990) 162, vol. 5., 1145–50.

Maki, D.G., et al.,"*An attachable silver–impregnated cuff for prevention of infection with central venous cathters; a prospective randomized multicenter trial,"*Am. J. Med (1988) 85 vol. 3, 307–14.

Norwood, S., et al., "*The influence of an attachable subcutaneous cuff for preventing triple lumen catheter infections in critically ill surgical and trauma patients,"*Surg. Gynecol Obstet (1992), 175, vol. 1, pp. 33–40.

* cited by examiner

DUAL MODE ANTIMICROBIAL COMPOSITIONS

FIELD OF THE INVENTION

The present invention relates to microbe resistant articles and compositions that are for internal or external use with humans or animals, and methods for making these articles and compositions.

BACKGROUND OF THE INVENTION

Articles such as medical devices may be classified according to their method of use, i.e. as those used for total implants or those used as access devices. The medical access devices may be further classified as those that exit at a bodily orifice, such as a Foley catheter, and those that exit transcutaneously, such as venous catheters. Medical devices such as catheters, which come into contact with bodily fluids and organs, are often left in place for prolonged periods of time. Several problems are encountered from the use of indwelling catheters such as the introduction of bacteria during insertion or implantation or upon long term exposure of the catheter exit site to the environment. In addition, long-term catheter use often develops biofilm on the catheter surface reducing patient comfort and contributing to the possibility of infection.

Attempts have been made to prevent microbial infection related to catheter use by bonding an antibacterial agent to a catheter. For example, U.S. Pat. No. 5,476,509 describes a catheter having a polymeric coating that has an antibiotic agent covalently or ionically bound thereto. Similarly, U.S. Pat. No. 5,798,115 describes a catheter having a polymer coating that has an antibiotic covalently bonded to the polymer backbone. While these catheters may kill bacteria that are kept in contact with it for prolonged periods of time, the catheter is not effective at killing bacteria that are introduced into the body during insertion of the catheter since the antibiotic is attached to the catheter and the bacteria are able to diffuse away from the catheter. A different type of catheter is described in U.S. Pat. No. 5,019,096. In this patent, a catheter having a matrix-forming polymer in which an antimicrobial agent is impregnated, is described. Since the antibiotic is not covalently or ionically bound to the polymer, it is able to diffuse away from the catheter. While this catheter may show some effectiveness against bacteria introduced during insertion of the catheter, the long term antibacterial effectiveness is limited as the antibacterial agent diffuses out of the polymer coating in a relatively short period of time. In addition, short-term, incomplete killing of bacteria, such as that resulting from impregnated catheters, has been shown to encourage bacterial resistance.

It is known that hydrophilic coatings with low friction (coefficient of friction of 0.3 or less) are useful for a variety of medical devices such as catheters, catheter introducers, guide-wires and the like. When low friction devices are used, the devices, upon introduction into the body, slide easily within the arteries, veins, and other body orifices and passageways. In some cases, the material of the catheter or medical device is formed of a material having good anti-friction properties such as poly(tetrafluoroethylene) or other plastics which tend to avoid abrasion with the body. However, in many cases the selection of material does not provide the anti-slip properties desired in conjunction with other desirable properties of the particular medical device. In other cases, the desired adherence of a lubricious coating to a particular substrate is not achieved. Thus, there exists a need for long-term, microbe resistant articles that do not enhance the likelihood of creating resistant infections and which have lubricious and durable surfaces.

SUMMARY OF THE INVENTION

This invention provides durable and lubricious compositions and articles that have a relatively potent short-term microbial resistance in addition to a sustained long-term microbial resistance. In addition, this invention provides methods for making microbially resistant compositions and articles wherein the compositions and articles have a relatively potent short-term microbial resistance and a sustained long-term microbial resistance and wherein the articles and compositions have a durable and lubricious surface.

In accordance with an embodiment of the invention, a composition is provided that is a multi-layer coating. The coating comprises a layer of metallic silver overlaid with a polymer, preferably a hydrogel, which contains an antimicrobial agent. In accordance with an additional embodiment of the invention, an article having a layer of metallic silver applied thereto which is overlaid with a hydrogel containing an antimicrobial agent is provided. Preferred articles for use according to the invention are medical articles. In particular, medical articles such as catheters are preferred. These articles have affixed to their surfaces a metallic silver layer which is covered by a hydrogel containing an antimicrobial agent. In accordance with a further embodiment of the invention, methods for producing the articles and the compositions of the invention are provided. The method comprises:

a) providing a layer of metallic silver b) preparing a coating solution by dissolving a polymer, preferably a hydrogel, or the components to produce a polymer or hydrogel in one or more solvents c) incorporating at least one antimicrobial agent into the coating solution; and d) coating the metallic silver layer with the coating solution containing the antimicrobial agent.

DETAILED DESCRIPTION OF THE INVENTION

Articles that embody the present invention generally can be any article that contacts patients or is used in health care. The articles may be for use either internally or externally, and include, for example, catheters, tubes, shunts, condoms, medical gloves, implants, sutures, grafts and the like. The articles can be made from a variety of natural or synthetic materials, such as, for example, latex, polystyrene, polyester, polyvinylchloride, polyurethane, ABS polymers, ceramics such as aluminum oxide, glass, polyamide, polimide, polycarbonate, synthetic rubber, stainless steel, silicone and polypropylene.

The metallic silver layer is formed by methods known in the art such as wet deposition, electroplating, sputter coating and vacuum deposition. A preferred method of forming the metallic silver layer is wet deposition as described in U.S. Pat. No. 5,395,651. The entire disclosure of U.S. Pat. No. 5,395,651 is incorporated herein by reference. Briefly, metallic silver is deposited upon the surface of an article using a multi-step wet deposition process. The surface is cleaned, and then activated in an aqueous solution containing tin. The silver is deposited from an aqueous solution of a silver-containing salt, a reduction agent that reduces the salt to form the metallic silver, and a deposition control agent that prevents the silver from nucleating throughout the solution. After the article is coated, the coating is stabilized as described in U.S. Pat. No. 5,395,651. The metallic silver layer can be between about 2 angstroms and about 10 microns. A preferred thickness is between about 2 angstroms and about 2,000 angstroms. Alternatively, the amount of silver deposited is determined by weight per unit area. The amount of silver deposited can be from about 0.1 $\mu g/cm^2$ to about 100 $\mu g/cm^2$. A preferred about of silver deposited per unit area is from about 0.5 $\mu g/cm^2$ to about 20 $\mu g/cm^2$.

Nearly any hydrophilic polymer can be used according to this invention. For example, a polyurethane coating which takes up about 10% by weight of water or less can be used. Polymer coatings which are water soluble can also be used. For example, polyvinylpyrrolidone (PVP), which dissolves off when wet, can be used. However, polymer coatings known as hydrogels are preferred. Hydrogels for use according to the invention are those polymers known in the art that exhibit about 25% by weight to about 500% by weight water uptake. Preferably, the hydrogels for use according to this invention exhibit about 50% by weight to about 200% by weight water uptake, and, more preferably, from about 75% by weight to about 150% by weight water uptake. The hydrogels may be derived from water-soluble polymers including, but not limited to, poly(ethylene oxide), poly (ethylene glycol), poly(vinyl alcohol), polyvinylpyrrolidone, poly(ethyloxazoline), polyamino acids, pseudopolyamino acids, as well as mixtures of these with each other or other water-soluble polymers. These water-soluble polymers are complexed with or covalently bound to a second polymer, for example, a polyurethane, a polyurea, a polyurethaneurea, as well as mixtures of these with each other or with other polymers. The second polymer can be added as a preformed polymer or it can result from the polymerization of monomers which are polymerized in the presence of the water-soluble polymer. The polymerization reaction can take place before or after coating the substrate. The second polymer may or may not be cross-linked. If the second polymer is cross-linked, a preferred amount of cross-linking is between about 50% to about 90% or greater. A preferred polymer for coating is a polyether polyurethaneurea block copolymer which is not cross-linked. For example, the polyether polyurethaneurea block copolymer known as D6/40 obtained from Tyndale Plains-Hunter, Ltd. is a preferred polymer.

Antimicrobial agents useful according to this invention include the biquanides, especially chlorhexidine, polymyxins, tetracyclines, aminoglycosides, rifampicin, bacitracin, neomycin, chloramphenicol, miconazole, quinolones, penicillins, nonoxynol 9, fusidic acid, cephalosporins, mupirocin, metronidazole, cecropins, protegrins, bacteriocins, defensins, nitrofurazone, mafenide, acyclovir (U.S. Pat. No. 5,744,151), vancomycins, clindamycins, lincomycins, sufonamides (U.S. Pat. No. 5,869,127), norfloxacin, pefloxacin, nalidixic acid, oxolinic acid (quinalone), enoxacin, ciprofloxacin, and fusidic acid (U.S. Pat. No. 5,019,096) and combinations thereof. A preferred antimicrobial agent is chlorhexidine, as it exhibits a synergistic effect with silver.

The antimicrobial agent is incorporated in the compositions of this invention in an amount that is effective at inducing microbial stasis or killing to produce microbial resistant compositions. Methods for determining microbial stasis or killing are know in the art and include, for example, measuring the minimum inhibitory concentration (MIC) of coated catheter extracts, zone of inhibition (ZOI) testing, and bacterial adherence testing, using known clinical pathogens for all tests.

A coating solution is prepared by dissolving a polymer or polymer components in a solvent. The solvent may be any organic solvent or combination of solvents that preferably includes a polar organic solvent. In addition, water may be used as a solvent either alone or as a mixture with organic solvents. An antimicrobial agent, preferably dissolved in a solvent, is then added to make the antimicrobial coating solution. For example, a hydrogel forming polymer such as a polyether polyurethaneurea is dissolved in a mixture of tetrahydrofuran (THF) and an alcohol to form a 3% weight/polymer solution. The ratio of THF to alcohol typically ranges from about 50% to about 100% THF. Chlorhexidine is dissolved in the same alcohol used to make the coating solution or in dimethylacetamide to form about a 5% solution by weight. The chlorhexidine solution is then added to the coating solution in an amount that produces a coating that contains about 1% to about 10%, preferably about 1% to about 5%, chlorhexidine based on the dry weight of the coating. The coating solution is then applied to a silver coated article by dip or spray coating techniques.

The superior and unexpected results obtained from the compositions, articles and methods of the present invention result from the dual modes of action resulting from two distinct antimicrobial layers. For example, when a catheter is inserted into a patient, there is a likelihood that microorganisms will be introduced along with the catheter. This sudden introduction of a relatively large number of microorganisms is suppressed by the chlorhexidine diffusing from the coating of the catheter. Once indwelling, the catheter continues to release chlorhexidine and prevent infection in the surrounding tissue. As the chlorhexidine becomes depleted, the surface of the catheter continues to be antimicrobial due to the metallic silver coating. Silver ions released from the metallic silver layer prevent microbial migration along the shaft of the catheter into the body. The continued presence of silver on the catheter surface and the slow release of silver ions not only prevents the attachment of bacteria, it also inhibits the development of biofilm. In fact, silver catheters with a polymer coating have been reported to delay the onset of urinary tract infections, in spite of their limited ability to kill bacteria on contact, as evidenced by the lack of zones in the ZOI test described below. In addition, the presence of silver ions weakens bacteria by a different mechanism from chlorhexidine, reducing the potential for the development of a resistant infection. Thus, the coatings of the present invention offer resistance to bacterial migration and growth resulting from the silver coating plus they offer additional resistance due to a rapid release of an antimicrobial agent which kills bacteria introduced upon insertion of the catheter.

The following examples are presented to illustrate the present invention, but are in no way to be construed as limitations on the scope of the invention. It will be recognized by those skilled in the art that numerous changes and substitutions may be made without departing from the spirit and preview of the invention.

EXAMPLES

Coating Compositions and Procedures

A silver layer was deposited upon the inside and the outside of a catheter made of latex (natural rubber) according to the following procedure. The latex catheter was cleaned by dipping it in a cleaning solution containing 1–5 percent of sodium hypochlorite, at ambient temperature for 2 minutes, followed by rinsing in demineralized water. The catheter was then dipped into an activating solution of 0.05 grams per liter of stannous chloride at ambient temperature for 10 minutes, followed by rinsing in demineralized water. Silver was deposited on the catheter by dipping it into a bath containing 0.01 grams per liter of silver nitrate, 0.10–0.12 grams per liter sodium nitrate, and sufficient ammonia to achieve a pH of from about 8.5 to about 9.5. Lastly, the silver layer was stabilized by dipping it in a 0.1% solution of platinum chloride in hydrochloric acid at a pH of about 4.1 for a time of 1 minute at ambient temperature.

A 3% polymer coating solution containing 3% (dry weight) of chlorhexidine was prepared by first dissolving 10.3 g of a polyether polyurethane-urea block copolymer (Tyndale Plains-Hunter) in 334.0 g tetrahydrofuran (THF). Next, a 5% solution of chlorhexidine was prepared by dissolving 0.31 g chlorhexidine in dimethylacetamide. The two solutions were then combined with stirring to form the final coating solution. Latex Foley catheters (16 Fr) which were previously silver coated as described above were then dipped into the polymer/chlorhexidine solution and removed at a constant rate to provide an even outer coating of lubricious, hydrophilic polymer containing chlorhexidine.

Lubricity

Upon contact with aqueous fluids, catheters coated as described above absorb moisture and become lubricious, or slippery, to the touch. The degree of lubricity of the coating was measured by a test of Coefficient of Friction (COF). In this test, a pair of catheters was positioned in a trough of water and a 400 g stainless steel sled wrapped with a cellulose membrane was pulled down the shafts of the pair of catheters. The force required to pull the sled was averaged over a length of the catheter, and this force was divided by the weight of the sled to give a unitless value of COF.

The COF for the catheters produced according to the methods described above averaged 0.06. A typical range of COF for the preferred hydrophilic coating of the invention is 0.02 to 0.15. The most preferred range of COF for coatings of the invention is 0.02 to 0.08.

Durability

The durability of coatings produced according to the methods described above and other hydrophilic coatings of the invention were determined in two ways. First, the catheters were tested for COF over a period of 21 days. In this test, catheters were incubated in deionized water at 37° C., and COF was measured after one hour, 1, 7, 14 and 21 days. The durability of the coating was then determined by the change in COF over the 21 day period. Coatings that change very little or increase their lubricity from the first to the 21$^{st}$ day of testing are considered durable. A second test of durability was to hold the hydrated, coated catheter in a wet hand and rub the thumb back and forth ten times on the coated shaft, traversing a distance of about one inch. The coating is considered very durable if it maintains its lubricity after ten rubs. A low durability coating rubs off in this test.

Microbial Resistance

Antimicrobial activity was determined by two methods, zone of inhibition (ZOI) and bacterial adherence (BA). For ZOI, one quarter inch segments of catheter were incubated in an agar culture of a test organism. After 24 hours, a measurement was made of the proximity of the bacteria to the surface of the catheter segment. If a sample released an antimicrobial agent, a ring containing no bacterial growth was evident around the catheter segment and the distance in millimeters from the catheter surface was defined as the zone of inhibition. In the ZOI test, catheters produced according to the methods above exhibited zones ranging from 1 to 5 mm for ten different test organisms. See Table 1. Control samples of catheters coated with silver and lubricious polymer but no chlorhexidine showed no zones of inhibition when tested against the ten test organisms.

Antimicrobial activity was also demonstrated for catheters coated according to the methods described above by bacterial adherence testing. In this test, catheter segments were incubated for 18 hours in a solution containing radio-labeled bacteria. The catheter segments were then rinsed and the number of organisms that adhered to the catheter segment was determined by scintillation counting. Coatings produced according to the present invention showed a significant decrease in the number of bacteria that adhered to the coating surface when compared to coatings simply having a lubricious coating over a silver layer for each of the ten clinically relevant bacteria shown in Table 1.

TABLE 1

Zone of inhibition testing on a Bardex IC Foley catheter coated according to the invention such that the coating comprised 2.9% chlorhexidine.

| Microorganism | Sample 1 | Sample 2 |
|---|---|---|
| *Candida albicans* (GSU-30) | 3 mm | 3 mm |
| *Citrobacter diversus* (koseri) | 4 mm | 4 mm |
| *Enterobacter cloacae* | 2 mm | 2 mm |
| *Enterococcus faecalis* (urine) | 3.5 mm | 4 mm |
| *Escherichia coli* (UTI) | 4.5 mm | 4.5 mm |
| *Klebsiella pneumoniae* (UTI) | 2 mm | 1.5 mm |
| *Proteus mirabilis* (UTI) | <1 mm | <1 mm |
| *Pseudomanas aeruginosa* (GSU-3) | 1.5 mm | 1 mm |
| *Staphylococcus saprophyticus* | 4 mm | 5 mm |
| *Enterococcus faecium* (UTI) | 4.5 mm | 4 mm |

We claim:

1. An article that resists microbial infection, the article having interior and exterior surfaces, the article comprising:
   a metallic silver layer on at least one of the surfaces of the article;
   a polyether polyurethaneurea block copolymer layer; and
   an effective amount of an antimicrobial agent incorporated into the polymer layer and being capable of diffusing from the polymer layer.

2. The article according to claim 1, wherein the copolymer layer is soluble in water.

3. The article according to claim 1, wherein the antimicrobial agent is a biquanide.

4. The article according to claim 3, wherein the biquanide is chlorhexidine.

5. A coated article comprising:
   an article having a plurality of surfaces; and
   a coating covering at least part of the surfaces,
   wherein the coating comprises:
      a silver layer deposited on at least part of one of the surfaces of the article; and
      an outer layer, covering the silver layer, comprising a durable and lubricious polyether polyurethaneurea block copolymer and an effective amount of an antimicrobial agent and,
   wherein the antimicrobial agent is capable of diffusing from the outer layer.

6. The article according to claim 5, wherein the article is comprised of a material selected from the group consisting of latex, polystyrene, polyester, polyvinylchloride, polyurethane, ABS polymers, ceramics, glass, polyamide, polyimide, polycarbonate, synthetic rubber, stainless steel, silicone and polypropylene.

7. The article according to claim 5, wherein the outer layer is soluble in water.

8. The article according to claim 5, wherein the antimicrobial agent is a biquanide.

9. The article according to claim 8, wherein the biquanide is chlorhexidine.

10. A method for producing a microbe resistant article comprising:
   a) depositing a layer of metallic silver on a surface of the article;
   b) preparing a coating solution capable of producing a coating by dissolving polymer or monomers which react to form polymer in solvent;
   c) incorporating at least one antimicrobial agent into the coating solution; and
   d) coating over the metallic silver layer with the coating solution containing the antimicrobial agent such that the antimicrobial agent is capable of diffusing from the coating, and where the polymer is a polyether polyurethaneurea block copolymer.

11. The method according to claim 10, further comprising contacting the metallic silver layer with at least a portion of at least one surface of an article.

12. The method according to claim 10, wherein the polymer is water soluble after coating.

13. The method according to claim 12, wherein the antimicrobial agent is a biquanide.

14. The method according to claim 13, wherein the biquanide is chlorhexidine.

15. A coated article comprising:
   a first antimicrobial agent disposed on a surface of the article; and
   a second antimicrobial agent disposed in a coating covering the first antimicrobial agent,
   wherein the first antimicrobial agent is a continuous surface-coated metallic silver that is capable of releasing silver ions and has a longer lasting antimicrobial activity than the second antimicrobial agent, and wherein the second antimicrobial agent is capable of diffusing from the coating more rapidly than the first antimicrobial agent.

16. The coated article according to claim 15, wherein the coating is a multi-layer coating.

17. The coated article according to claim 16, wherein the coating comprises a metallic silver layer and a durable and lubricious polymer layer.

18. The coated article according to claim 17, wherein the polymer layer is a hydrogel polymer.

19. The coated article according to claim 15, wherein the antimicrobial agent is a biquanide.

20. The coated article according to claim 19, wherein the biquanide is chlorhexidine.

21. The article according to claim 5, wherein the coated article contacts a patient.

22. The article according to claim 21, wherein the coated article is for internal use.

23. The article according to claim 22, wherein the coated article is a catheter.

24. The article according to claim 1, wherein the article is a catheter.

25. The article according to claim 24, wherein the article is a latex article.

26. The article according to claim 5, wherein the article is a catheter.

27. The method according to claim 10, wherein the article is a catheter.

28. The method according to claim 27, wherein the catheter is a latex catheter.

29. An article comprising:
   a catheter having exterior and interior surfaces, the catheter being made of a polymer selected from a group consisting of:
   latex and silicone;
   a metallic silver layer deposited on at least one of the catheter surfaces, the layer having a thickness between about 2 angstroms and about 10 microns;
   a polyether polyurethane-urea block copolymer coating disposed to cover the metallic silver layer; and
   chlorhexidine, in an amount between about 1% to about 10% based on the dry weight of the block copolymer coating, releasably disposed within the block copolymer coating.

30. The method of claim 18, wherein preparing a coating solution comprises dissolving polymer or monomers which react to form polymer in an aqueous solvent.

31. The method of claim 10, wherein depositing a layer of metallic silver on a surface of the article comprises carrying out a reduction reaction to deposit silver on the surface.

32. The method of claim 31, wherein the step of carrying out a reduction reaction comprises:
   cleaning the surface of the catheter;
   activating the surface of the catheter;
   forming the metallic silver layer on the article by dipping the article into a bath having a silver salt such that the silver salt is reduced to a metallic silver layer that is deposited on the surface of the catheter; and
   stabilizing the metal silver layer.

33. An article having a plurality of surfaces and comprising:
   a coating including
   (1) a silver layer deposited on at least part of one of the surfaces of the article,
   (2) a hydrogel polymer layer covering the silver layer, and
   (3) an effective amount of an antimicrobial agent disposed within the hydrogel polymer layer and capable of diffusing therefrom.

34. A method of producing a microbe resistant article, the method comprising:
   a) cleaning and activating a surface of the article;
   b) forming a metallic silver layer on the activated surface by dipping the article into a bath having a silver salt that is reduced to form a metallic silver layer on the activated surface;
   c) stabilizing the metallic silver layer; and
   d) coating the metallic silver layer with a polymer solution comprising at least one antimicrobial agent such that the antimicrobial agent is capable of diffusing therefrom.

* * * * *